United States Patent [19]

Barer

[11] 4,047,925
[45] Sept. 13, 1977

[54] ALKANE DIOLS AS CHEMICAL PINCHING AGENTS

[75] Inventor: Sol J. Barer, Clark, N.J.

[73] Assignee: Celanese Corporation, New York, N.Y.

[21] Appl. No.: 621,893

[22] Filed: Oct. 14, 1975

[51] Int. Cl.$^2$ .............................................. A01N 9/24
[52] U.S. Cl. .......................................... 71/78; 71/76; 71/122
[58] Field of Search ............................. 71/78, 122, 76

[56] References Cited
U.S. PATENT DOCUMENTS 2,801,160   7/1957   Iserson .................................... 71/70

OTHER PUBLICATIONS

Yoshitan, et al., Chem. Abst., vol. 73, (1970), 53110z.
Morre et al., Chem. Abst., vol. 63, (1965), 10589b.

Primary Examiner—Lewis Gotts
Assistant Examiner—Catherine W. Mills

[57] ABSTRACT

Chemical pruning, and contact compositions for the selective inhibition of suckering in plant species subject thereto, particularly tobacco, said compositions comprising as an active species a lower alkane diol, especially 1,3-butanediol.

9 Claims, No Drawings

ALKANE DIOLS AS CHEMICAL PINCHING AGENTS

BACKGROUND OF THE INVENTION

Certain species of plants exhibit at least in the mature stages a tendency to suckering i.e. the formation of subordinate shoots spring from a bud on the stem, so-called axillary buds. This secondary growth has the effect of subverting the maturation of blossoms, fruit, or leaves for ultimate harvesting and is accordingly desirously avoided in cultivation. This tendency is particularly pronounced in the tobacco plant, especially in the maturation stage following topping or decapitation, i.e. the removal of the terminal growth, main leader or stem apex. In other cases, topping or removal of apical meristematic tissue is itself desirably accomplished chemically.

Large leaf tobaccos as grown in the United States have typically been topped at or shortly after flowering, when dark air cured and fire cured types may have 10 to 16 leaves and burley, flue-cured, Maryland or cigar types may have 16 to 20 leaves. Tops (the blossoms) in tobacco tend to supress sucker growth down the stalk, so when tops are removed rapid and profuse sucker growth occurs at the juncture of the stem and each leaf thus limiting the development of the upper leaves which are by far the most profitable. Also, suckers provide food for young budworms and hornworms in addition to supplying a preferred site for hornworm egg laying. Accordingly, sucker control is essential for commercial cultivation. It is also important for efficient harvesting, as current mechanical harvesters require near-perfect sucker control for proper operation.

Recently, earlier topping in the button stage has been employed as a means of increasing yields and affording better pest control. The resultant increased tendency to sucker had been controlled in the past by hand removal as often as 3 times in one season. Most recently, control has been achieved by the use of contact chemical control agents, such as methyl caproate in combination with a later application of a systemic agent such as maleic hydrazide which controls subsequent secondary growths. Successful sucker control permits most of the plant resources to be directed into making larger and heavier leaves, with sufficient spread to have desirable quality.

Various contact chemical agents have been tested for improved sucker control including dimethyldodecylamine acetate ('Penar' manufactured by Pennwalt), 1-octanol/1-decanol mixtures ($C_6$-$C_{12}$) (available, for example as Off-Shoot-T from Proctor and Gamble Co.) the lower alkyl esters of fatty acids (available as Off-Shoot-O from Procter and Gamble Co.) and Emgard from Emery Industries, Inc.) and methyl pelargonate (T-61, available from Emery Industries). See Tobacco Science XIV, pp. 65–68 (1970) and XVI, pp. 134–135 (1972). Although results of testing vary, the dual use of the higher fatty alcohol/maleic hydrazide systems proved superior in testing as reported in Tobacco Science XIV, pp. 86–88 (1970), resulting in the lowest sucker numbers and weight per plant with destruction of the primary and secondary buds in the leaf axils contacted.

A more detailed study of the higher fatty alcohol systems in J. Agri. Food Chem. Vol. 15, No. 16, pp. 972-5 (1967) showed that the $C_9$-$C_{11}$ species were highly active, more so than the corresponding higher fatty acid methyl ester, whereas higher or lower fatty alcohols were relatively inactive.

The higher fatty alcohols and derivatives thereof are in somewhat short supply, and are relatively expensive. Also such systems require the proper type and amount of surfactant to control translocation and avoid nonselective tissue kill.

In addition to the fatty alcohols (U.S. Pat. No. 3,824,094) the lower alkyl esters thereof (U.S. Pat. No. 3,340,040; Canada 968,176) or the combination thereof with an N-carbamate (U.S. Pat. No. 3,438,765 and 3,326,664), the patent literature also evidences as chemical pinching agents glycol esters of fatty acids (U.S. Pat. No. 3,900,351); combinations of diethylene glycol monobutyl ether and hydrocarbyl ether derivatives (U.S. Pat. No. 3,713,804); and alcohol/glycol esters of styrene-maleic anhydride copolymers (U.S. Pat. No. 3,697,250 or U.S. Pat. No. 3,556,763) in the last of which there is compared the performance of polyalkylene glycol ethers.

In the case of certain of these chemical agents consequential metabolic changes are induced in the product leaf considered to lower the quality of the tobacco. In other cases, there is evidence of undesirable residues being imparted to the leaf. In still further instances, topical application may involve chlorosis, necrosis or distortion of leaf structure, nodal scars or stem burn.

Accordingly, the development of new and improved contact compositions for control of meristematic tissue at reasonable expense is desired, especially for effective control with minimum damage to the cultivar.

BRIEF DESCRIPTION OF THE INVENTION

It has now been discovered that lower alkane diols are effective chemical pruning, pinching or disbudding agents, in the control of meristematic tissue and the enhancement of spreading growth in the plant species exhibiting suckering or a growth pattern typically controlled by pruning of meristematic tissue, including tobacco, tomato, azalea, crysanthemum, soybean and cotton. Effective control is achieved with these contact compositions without significant plant injury or distortion i.e. the phytotosis or necrosis in meristematic tissue is essentially selective.

These systems are particularly valuable because the active agents, especially 1,3-butanediol, is water soluble, and of low toxicity and volatility. Further, control may be achieved without significant plant injury even in the absence of a surfactant adjuvant.

The remarkable effectiveness of the systems of the invention is all the more surprising when it is recalled that prior research reported the lower fatty alcohols such as 1-butanol, for example, to exhibit little or no utility in the control of tobacco suckering.

Although such lower alkane diols are known for use as humectants (see, e.g. U.S. Pat. Nos. 1,407,274 and 3,000,764-5) with tobacco, and have some other known usage in agricultural compositions as diluents, antifreeze components, etc., there has been no recognition of the use as a principal active agent for growth control of plant tissue and, indeed, contraindicatory evidence such as the absence of plant response shown for 1,3 butanediol in attempted defoliation of cotton plants. (U.S. Pat. No. 2,801,160)

The practice of this invention is represented primarily by the control of suckering in tobacco plants because of its economic significance and for simplicity of description. However, it is found that the lower alkane diols are generally effective in the control of meristematic tissue for plant species requiring such growth control in apical or axillary shoots or buds when applied topically; and no serious adverse effects on plant growth or maturation is seen in other portions of the plant or by washing into the soil;

As the lower alkane diols there are included the $C_2$–$C_6$ branched or straight chain structures including ethylene glycol; 1,2 propanediol; 1,3-butanediol; 1,4-butanediol; 2,3-butanediol; 2-methyl-1,2-propanediol; 2-methyl-1,3-propanediol; 1,3-propanediol; etc. The $C_3$–$C_4$ species are preferred.

The utilization of these active agents alone or in combination with other materials is substantially in accordance with art technique as embodied for example in the method of U.S. Pat. No. 2,720,451. The alkane diols are water soluble and, accordingly, may be applied to the plants from aqueous solution e.g. as a spray, although of course may also form part of an emulsion system where oily components are included, or even be included in a paste or foam.

The concentration of alkane diol in the contact composition should range from about 2.5 to about 50% usually 5% to 25% preferably 10–15% for most uses. Concentrates will conveniently incorporate a higher percentage up to high purity alkane diol, but ordinary dilution in conventional spray equipment will result in an ultimate application of an average of about 0.3 to about 15, preferably 1.35 to 13.5 ml. of active diol component to each plant.

Obviously, conditions of application such as temperature, humidity, wind and rain; stage of growth; and plant species will be considered in the individual case. Typically, an aqueous solution of appropriate concentration is prepared and a spray is directed to the top of the plants to the point of runoff. A gallon of spray typically covers about 120 tobacco plants, or expressed otherwise the coverage represents the application of 20–100 lbs of active agent per acre of cultivated tobacco. Finer sprays are preferred for foliar application, while a coarse spray will ordinarily be found most useful for contact treatment.

Time of application is related to bud growth and prior manual or chemical pinching if any. Commonly, manual or mechanical pinching or topping is carried out first, followed by chemical pinching at an interval which may range from 1–3 days up to 8 weeks. Where the primary pinching is carried out chemically, application is made just before to just after bud development to insure best results at reasonable concentrations.

In the case of tobacco, which is manually or mechanically topped in the early button or blossoming stage, a spray of 250,000 ppm 1,4-butanediol applied topically to the stem has been found effective in the control of suckers, in one case providing 85% control (by weight).

As mentioned earlier, the destruction of apical meristematic tissue tends to stimulate spreading growth by the development of new shoots. In certain species this is a desirable phenomenon and, indeed, the object of the pinching process. Such plants as azaleas or crysanthemums are typical where control of meristematic tissue leads fo spreading growth for better shape or density, and resultant increased blossom profusion. The application in this manner of 2.5 to 10% of an aqueous solution of 1,3-butanediol to Gloria and Red-wing azaleas according to the invention provided breaks/shoot equivalent to the commercial Off-Shoot-O agent (methyl decanoate).

DETAILED DESCRIPTION OF THE INVENTION

In the practical application of the invention it is both convenient and economical to take advantage of the most inexpensive and readily available glycol of favorable ecological properties and for these purposes 1,3-butanediol is preferred.

The active agent is a liquid of low toxicity and volatility and may be stored indefinitely without physical, chemical or biological degration. Concentrates may be readily prepared, at any level of glycol in water or other diluent. It is understood that mixtures in all proportions of the $C_2$–$C_6$ alkane diols is contemplated, and certain of such mixtures may be preferred for selected applications. Commonly, an aqueous solution or emulsion of concentrated agent is prepared for dilution with water in a spray device for such purpose. Where surfactant is employed as desired, the spray may actually form a foam of benefit in localizing the agent. It is, of course, possible to admix the $C_2$–$C_6$ alkane diols with other agents for sucker control or regulation of meristematic tissue, such as tertiary or secondary fatty amine, fatty acid ester or fatty alcohol contact agents; or the systemic agents such as maleic hydrazide. Somewhat less conveniently for mass application, the agent may also be provided as a paste or grease as by compounding with soaps or other thickening agents such as silicas, modified clays, etc.

Although the growth control agent is commonly applied to tobacco after topping, it is also possible to effect simultaneous topping and agent application as by utilizing the Clip-Oil device described in Information Series Bulletin No. 3, Oct. 1950, Dept. Agr. Eng., N.C. Agr. Exp. Station. The agent may be applied, however, within 1–3 days and may be reapplied 10–21 days later as needed. More commonly, the initial chemical pinching is followed within 7–14 days with an application of maleic hydrazide.

The rate of mass application is usually 20 to 100 lbs. per acre of cultivar as an aqueous spray of 5 to 50% growth control agent, or 1.35 to 13.5 ml. per plant. Somewhat greater amounts (up to 2x) are of course involved with foliar application.

The alkane diol may be diluted with any essentially inert liquid, and some advantage may be seen in admixtures with the alcohol corresponding to the diol. Where desired, any wetting agent, emulsifier or surfactant may be used although unlike certain other sucker control agents, potentiation with surfactants is not required. Suitable surfactants may be selected from the anionic, cationic and nonionic types including primary, secondary and tertiary alkyl amines, ethoxylated alcohol sulfates, alkyl sulfates, water soluble salts of a sulfonated alkyl, alkylbenzene, or alkyl glycerol ether, quaternary ammonium salts, quaternary imidazolinium salts, alkyl pyridinium salts, dialkyl morpholinium salts, ethoxylated fatty acids and/or sorbitol esters etc. Preferred ar the sorbitan fatty acid esters and the ethoxylated derivatives, ethers of polyoxyethylene glycol, and fatty acid esters of polyethylene glycol.

The amount of surfactant may range from the ordinary low level of 0.1 to 2.0% up to that commonly used with sucker control agents i.e. 25 to 50% by weight of the active agent.

It is of course also possible to combine the application of sucker control agent with other plant agents including fertilizers, herbicides, fungicides, insecticides, rodenticides, miticides, sterilants, minerals, hormones, pheromones, and like materials commonly used in agriculture for the maintenance or nurture of plant life, or the control or eradication of pests or desease therein, or the presence of undesired species thereabout. In fact, the alkane diol aqueous solution or emulsion may serve as a vehicle for such additives. 1,3-butanediol is preferred where water insoluble materials are incorporated as it is mutually soluble in water and such organics as acetone, castor oil, dibutyl phthalate, ethanol and methyl ether ketone, and preforms well as a coupling agent in emulsions.

In the following Examples and in the foregoing description, reference is made to contact application, by which is meant the direct contact of the active composition with the tissue for growth suppression or necrosis as by hand applying to suckers, or dripping agent down the stem. Foliar application refers to a general aerial spray to which the entire surface area of the plant is exposed. Reference to meristematic tissue is inclusive of terminal and axillary buds.

Nicotiana glutinosa is exemplified without limitation, it being understood that the invention has applicability to all tobacco types, including nicotiana tabacum and nicotiana rustica as well as the treatment of other ornamental and agricultural species including herbaceous plants such as ageratum, coleus, cotton, marigold, peanut, snapbean, snapdragon, soybean and tomato; semi-woody plants such as carnation, crysanthemum, forsythia, geranium, hydrangea and poinsetta; and woody plants such as apple, azalea, chamaecyparis, elm, euonymus, juniper, kolkwitzia, ligustrum, lonicera, maple, paper birch, pyracantha, taxus, weigela and pear For the preferred tobacco species, it may be observed that the tobacco plant, and particularly the leaves for harvest, are unimpaired in quality, exhibit a high retained filling value, and can be converted to products of excellent aesthetic properties. Further, since the alkane diols, principally 1,3-butanediol, are presently in use as humectants on tobacco, no new ingredient is introduced to the smoke chemistry, for example. 1,3-butanediol on tobacco offers the further advantage of biocidal mold inhibition.

EXAMPLE I 1,3-butanediol (Celanese, purity 99% min.) was formulated in deionized water to concentrations of 1000, 10,000, 100,000 and 1,000,000 ppm. Suckers on a set of tobacco plants (nicotiana glutinosa), topped in the button stage immediately prior to treatment were subjected to a contact spray from a hand held atomizer dribbled down the length of the stem. The application rate was about 4 ml. per plant (or at 100000 ppm, about 0.4 ml. active agent per plant). The following results of two replicates were obtained, in comparison to a commercial systemic control agent, maleic hydrazide and an untreated control, 14 days after treatment:

| 1,3-butanediol ppm. | Sucker Injury Ratings |
|---|---|
| 1,000,000 | 10 Ne, 10 Ne |
| 100,000 | 10 Ne, 10 Ne |
| 10,000 | 0, 0 |
| 1,000 | 0, 0 |
| Systemic Agent 5000 ppm | 3R, 5R |
| Control | 0, 0 |

Injury rating scale is from 0 (no effect) to 10 (sucker death); Ne represents necrosis, and R is retardation. 1,3 BG applied as a foliar spray (app. 8 ml solution/plant) with unprotected axillary suckers gave similar results.

EXAMPLE II

Tobacco (nicotiana glutinosa) plants in early (button) flowering stage were topped by removal of the terminal growing point.

The selective phytotoxicity of 1,3-butanediol to meristematic tissue was displayed by formulating 1,3-butanediol and n-octanol in several concentrations in deionized water and applied as sprays (to incipient runoff) to the foliage of tobacco plants (in three replicates) whose axillary suckers were protected from direct spray contact by covering with cotton plugs. The protective cotton plugs were removed from the air dried plants, and the specimens observed for injury, particularly to the suckers. The following results were obtained, in comparison to a meleic hydrazide standard, and an untreated control, 14 days after treatment:

| 1,3-butanediol, ppm. | Sucker Injury | Plant Injury |
|---|---|---|
| 250,000 | 3 Ne, 4 Ne, 4 Ne | 2 Ne, 0, 1 Ne[(1)] |
| 100,000 | 0, 0, 0 | 0, 0, 0 |
| 50,000 | 0, 0, 0 | 0, 0, 0 |

| N-octanol, ppm. | Sucker Injury | Plant Injury |
|---|---|---|
| 250,000 | 0, 0, 0, | 7Ne, 3Ne, 0 |
| 100,000 | 0, 0, 0, | 8Ne, 4Ne, 1Ne |
| 50,000 | 0, 0, 0, | 6Ne, 2Ne, 1Ne |
| MH 30 5000 | 3CLR, 3CLR, 3CLR | 0, 0, 0 |
| Control | 0 0 0, | 0, 0, 0 |

[(1)] Slight plant injury due to collected droplets of agent in depressed areas of leaf.
[(2)] Cl represents chlorosis; Ne is necrosis; and R is retardation.

The 30-40% control achieved with the 1,3 BG at 250,000 ppm evidences systemic translocation from the foliar area of application to the axillary sites of sucker development. At 250,000 ppm n-octanol induced moderate injury within one hour after application and this had increased to 6-8 Ne by 14 days, typical of contact type necrosis. Sucker response to the agents 14 days after treatment was also measured, as reported below:

| 1,3 Butanediol, ppm. | Terminal length, cm. | Sucker wt(g)/ Plant |
|---|---|---|
| 250,000 | 2.0, 4.5, 1.5 | 0.6, 0.1, 0.1 |
| 100,000 | 4.5, 3.0, 2.5 | 0.4, 0.6, 0.3 |
| 50,000 | 2.0, 3.0, 2.0 | 0.2, 1.1, 0.9 |
| N-octanol | | |
| 250,000 | 2.0, 2.5, 1.5 | 1.4, 1.3, 0.6 |
| 100,000 | 3.0, 2.0, 2.5 | 0.5, 0.6, 0.3 |
| 50,000 | 4.0, 2.0, 2.5 | 0.4, 0.4, 0.6 |
| MH 30(diethanolamine salt of 6-hydroxy-3-(2H)-pyridazinone) | | |
| 5000 | 0, 1.5, 0 | 0.1, 0.2, 0.1 |
| Control | 3.5, 4.0, 3.5 | 0.6, 0.4, 0.5 |

Injury induced by n-octanol even at intermediate levels to the foliage and suckers was sufficient to preclude further development of the suckers involved, and basal suckers appeared stimulated.

EXAMPLE III

The procedure of Example II was repeated, utilizing a contact spray application of about 4 ml per plant of a 1,3 butylene glycol solution in dieonized water containing 0.05% of a polyoxyethylene (20) sorbitan monolaurate (Tween 20) surfactant in comparison to the foliar application technique utilizing about 6-8 ml per plant.

The results which follow were recorded 21 days after treatment.

| Conc., ppm. | % Control, sucker weight[1] | | Avg. Length(cm), terminal suckers | | Avg. Sucker Weight (gm) | |
|---|---|---|---|---|---|---|
| | Foliar | Contact | Foliar | Contact | Foliar | Contact |
| 250,000 | 60.9 | 85.9 | 2.8 | 3.0 | 0.061 | 0.022 |
| 100,000 | 43.6 | 39.7 | 3.7 | 4.0 | 0.088 | 0.094 |
| 50,000 | 35.9 | 0.0 | 5.0 | 4.0 | 0.100 | 0.156 |
| Control | — | — | 3.8 | 3.8 | 0.930 | 0.930 |

[1]Sucker weights based upon 6 uppermost suckers per plant, utilizing 3 replicate plants per unit of treatment The only foliar injury perceived (1.3Ne) was in connection with foliar application at a 250,000 level.

Contact spray application was superior at higher agent concentrations, and evidenced no plant injury.

EXAMPLE IV

Ethylene glycol, 1,2-propanediol, and 1,4 butanediol were competitively tested for sucker control, in accordance with the technique of Example II (no surfactant) in both foliar and contact applications, with the following results recorded 21 days after treatment:

| | % Sucker Control[1] | | Length(cm) Terminal Suckers | | Avg. Sucker Weight (gm)[1] | |
|---|---|---|---|---|---|---|
| | Foliar | Contact | Foliar | Contact | Foliar | Contact |
| Ethylene Glycol | | | | | | |
| 250,000 | 18.0 | 96.2 | 3.8 | 3.8 | 0.128 | 0.022 |
| 100,000 | 29.9 | 32.1 | 4.8 | 3.3 | 0.111 | 0.094 |
| 50,000 | 39.7 | 39.7 | 3.7 | 2.7 | 0.094 | 0.156 |
| 1,2 Propanediol | | | | | | |
| 250,000 | 7.7 | 78.9 | 3.3 | 3.0 | 0.144 | 0.033 |
| 100,000 | 3.8 | 46.8 | 5.0 | 2.5 | 0.150 | 0.083 |
| 50,000 | 78.9 | 7.7 | 2.3 | 3.7 | 0.033 | 0.144 |
| 1,4-Butanediol | | | | | | |
| 250,000 | 27.8 | 85.9 | 2.7 | 2.0 | 0.122 | 0.022 |
| 100,000 | 0.0 | 77.1 | 3.3 | 1.8 | 0.156 | 0.050 |
| 50,000 | 0.0 | 0.0 | 4.3 | 3.8 | 0.206 | 0.161 |
| n-octanol | | | | | | |
| 75,000 | 0.0 | 0.0 | 2.7 | 4.0 | 0.167 | 0.183 |
| 50,000 | 0.0 | 18.6 | 3.5 | 3.2 | 0.172 | 0.127 |
| 25,000 | 32.1 | 0.0 | 3.7 | 3.8 | 0.160 | 0.200 |
| Control | | | 3.8 | 3.8 | 0.930 | 0.930 |

All diol agents were effective, especially by contact application in higher concentration. n-Butanol, tested in the same series, was totally ineffective.

EXAMPLE V 1,3-Butanediol as a solution in deionized water including 0.05% polyoxyethylene (20) sorbitan mono- laurate (Tween 20) surfactant was competitively tested in foliar and contact application against aqueous solutions of n-decanol (25% Tween 20 based on n-decanol) with the following results recorded 20 days after treatment:

| | % Control, Sucker Length[1] | |
|---|---|---|
| 1,3-Butanediol, ppm. | Foliar | Contact |
| 250,000 | 22 | 89 |
| 100,000 | 39 | 55 |
| 50,000 | 22 | 11 |
| n-decanol | | |
| 75,000 | 78 | 22 |
| 50,000 | 39 | 22 |
| 25,000 | 22 | 5 |
| MH-30 | 72 | 72 |
| Control | 0 | 0 |

[1]Based upon 6 uppermost suckers on each of 3 replicate plants.

Slight injury to the plants occurred only with foliar application. 1,3-butanediol was more effective in contact application at 100000 ppm and above, even comparing favorably to MH.30.

EXAMPLE IV

A series of azalea plants (24 Gloria and 24 Red Wing) were treated with an aqueous contact spray of 1,3-butanediol in comparison to Off-Shoot-O (methyl decon ate) and manual pinching. The results, as follows, are expressed as the average number of breaks per shoot:

| | Conc. | Gloria | Red Wing |
|---|---|---|---|
| Off-Sheet-0 | 4.2% | 2.01 | 2.02 |
| 1,3-Butanediol | 5.0% | 2.48 | 2.04 |
| | 7.5% | 2.13 | 2.07 |
| | 10.0% | 2.28 | 2.22 |
| Manual | | 2.31 | 2.18 |

Other exemplary aspects of the invention involve particularly treatment of crysanthemum, soybean and cotton plants in the same manner. Constructive compositions comprising combinations of e.g. higher fatty alcohols and esters thereof and the lower alkane diols in all proportions are contemplated in aqueous or water-lower alkanol solutions or emulsions. In view of the generally lower phytotoxicity of the alkane diols, it is expected that effective sucker control agents may be extended with these materials to advantage, and at low expense.

We claim:

1. A method for the inhibition of suckering in growing plants susceptible thereto comprising the application of an amount of a composition comprising an active agent consisting essentially of an alkane diol having 2 to 6 carbon atoms inhibitory to the growth of meristematic tissue.

2. The method of claim 1, wherein said alkane diol is selected from the group consisting of ethylene glycol, 1,2-propanediol, 1,3-butanediol and 1,4-butanediol.

3. The method of claim 1 further comprising applying said composition selectively to the suckering zone.

4. A method for the inhibition of secondary growth in growing topped tobacco plants comprising applying topically an effective amount of an alkane diol of 2 to 6 carbon atoms.

5. The method of claim 4, wherein said alkane diol is a butanediol.

6. The method of claim 4, wherein said alkane diol is applied in aqueous solution at a concentration of 2.5 to 50% by weight and a rate of about 20 to 100 lbs. per acre of cultivated tobacco.

7. A method for the inhibition of secondary growth in growing azaleas comprising applying topically an effective amount of an alkane diol of 2 to 6 carbon atoms.

8. In the inhibition of plant growth by topical application of chemical agent to meristematic tissue, the improvement which comprises the utilization of an effective amount of a composition consisting essentially of an alkane diol having 2 to 6 carbon atoms 9. The method of claim 1, wherein said composition also comprises a surface active agent.

* * * * *